US010549066B2

(12) United States Patent
Kaneko

(10) Patent No.: US 10,549,066 B2
(45) Date of Patent: Feb. 4, 2020

(54) DEVICE FOR REHABILITATION, REHABILITATION SYSTEM PROVIDED THEREWITH, PROGRAM FOR REHABILITATION AND REHABILITATION METHOD

(71) Applicant: KEIO UNIVERSITY, Tokyo (JP)

(72) Inventor: Fuminari Kaneko, Sapporo (JP)

(73) Assignee: KEIO UNIVERSITY, Tokyo (JP)

(*) Notice: Subject to any disclaimer, the term of this patent is extended or adjusted under 35 U.S.C. 154(b) by 83 days.

(21) Appl. No.: 15/301,796

(22) PCT Filed: Mar. 30, 2015

(86) PCT No.: PCT/JP2015/059851
§ 371 (c)(1),
(2) Date: Oct. 4, 2016

(87) PCT Pub. No.: WO2015/152122
PCT Pub. Date: Oct. 8, 2015

(65) Prior Publication Data
US 2017/0113015 A1 Apr. 27, 2017

(30) Foreign Application Priority Data
Apr. 4, 2014 (JP) .................................. 2014-077972

(51) Int. Cl.
A61M 21/00 (2006.01)
A61B 5/0482 (2006.01)
(Continued)

(52) U.S. Cl.
CPC ........... *A61M 21/00* (2013.01); *A61B 5/0261* (2013.01); *A61B 5/0482* (2013.01);
(Continued)

(58) Field of Classification Search
CPC ... A61B 5/1114; A61B 5/1121; A61B 5/1122; A61B 5/1124–1128; A61B 2505/09
See application file for complete search history.

(56) References Cited

U.S. PATENT DOCUMENTS
2010/0130893 A1   5/2010   Sankai

FOREIGN PATENT DOCUMENTS
JP   2007-020835 A   2/2007
JP   2008-264509 A   11/2008
(Continued)

OTHER PUBLICATIONS
Machine translation of JP 2007020835A.*
(Continued)

Primary Examiner — Carrie R Dorna
(74) Attorney, Agent, or Firm — Muncy, Geissler, Olds & Lowe, P.C.

(57) ABSTRACT

[Problem to be Solved]
To provide a device for rehabilitation capable of giving a patient who cannot express an intention to voluntarily move the body a kinesthetic illusion that the his/her own body is moving and thus achieving a high rehabilitation effect, a rehabilitation system including it, a program for rehabilitation, and a rehabilitation method.
[Solution]
The device for rehabilitation includes: a biological signal acquisition unit 71 that acquires biological signals from a patient imparted with illusory stimulation for inducing a kinesthetic illusion; a characteristic biological signal detection unit 72 that analyzes the biological signals and detects a characteristic biological signal indicating a state where the kinesthetic illusion is induced; and a control signal output unit 73 that outputs control signals for controlling body (Continued)

driving means 4 and/or brain simulating means 5, when the characteristic biological signal is detected.

17 Claims, 13 Drawing Sheets

(51) Int. Cl.
*A61B 5/0488* (2006.01)
*A61B 5/11* (2006.01)
*A61B 5/026* (2006.01)

(52) U.S. Cl.
CPC .......... *A61B 5/0488* (2013.01); *A61B 5/1121* (2013.01); *A61B 5/1128* (2013.01); *A61B 2505/09* (2013.01); *A61B 2562/0219* (2013.01); *A61M 2021/005* (2013.01); *A61M 2021/0022* (2013.01); *A61M 2205/3303* (2013.01)

(56) References Cited

FOREIGN PATENT DOCUMENTS

| JP | 2009082209 | * | 4/2009 | ............... A61B 5/11 |
| JP | 4618795 | B2 | 1/2011 | |
| JP | 2012-217721 | A | 11/2012 | |

OTHER PUBLICATIONS

Fuminari Kaneko, 1. Plasticity of brain due to therapeutic intervention other than exercise and its future possibilities, PT Journal, vol. 42, No. 12, Dec. 2008, p. 1017-1025 (partial translation of line 8, right column, p. 1022—line 1, right column, p. 1023 is attached).
F. Kaneko, et al, Kinesthetic Illusory Feeling Induced by a Finger Movement Movie Effects on Corticomotor Excitability,Neuroscience, vol. 149, issued 2007, p. 976-984.
International Search Report of PCT/JP2015/059851.

* cited by examiner

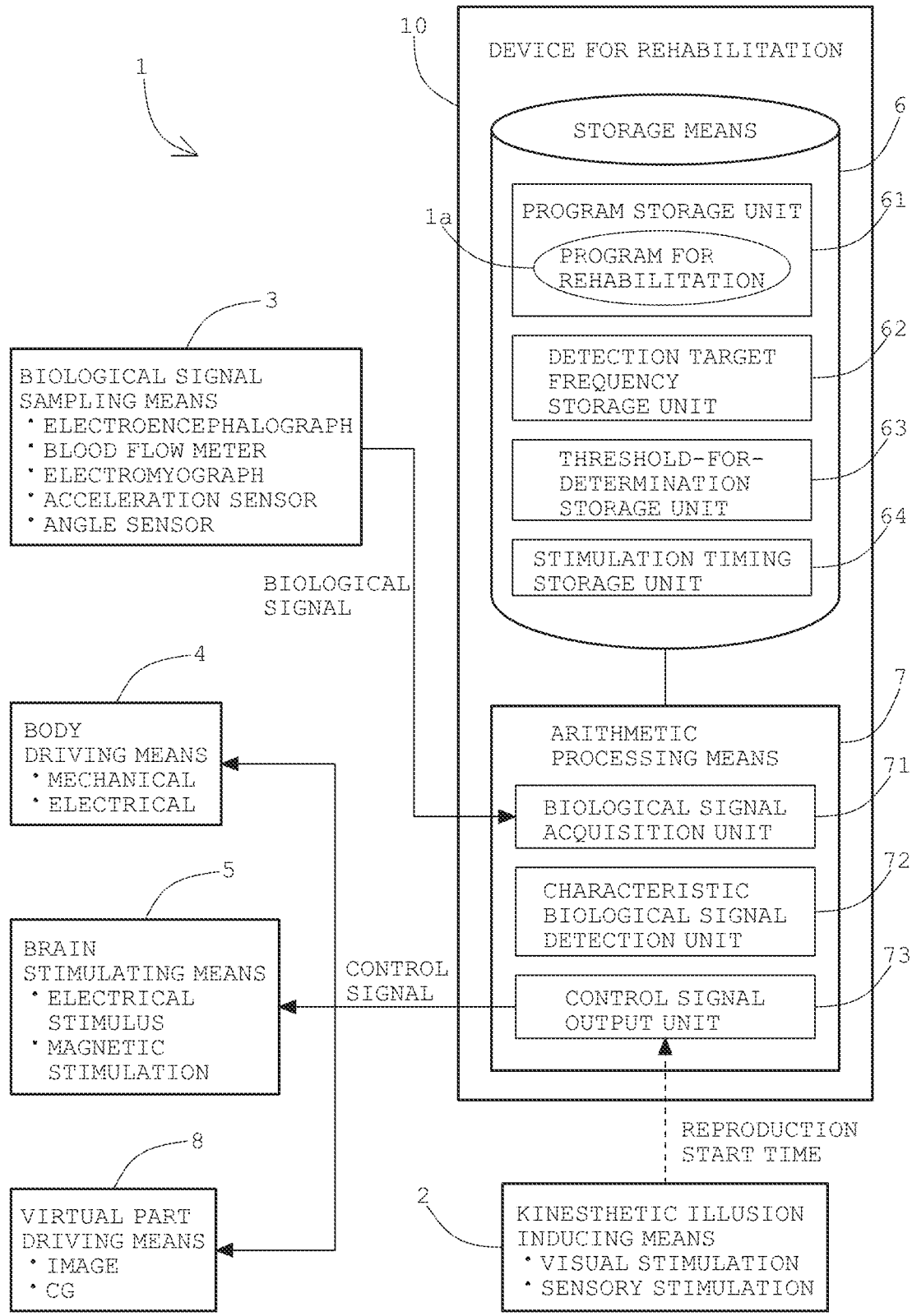
[FIG. 1]

[FIG. 2]
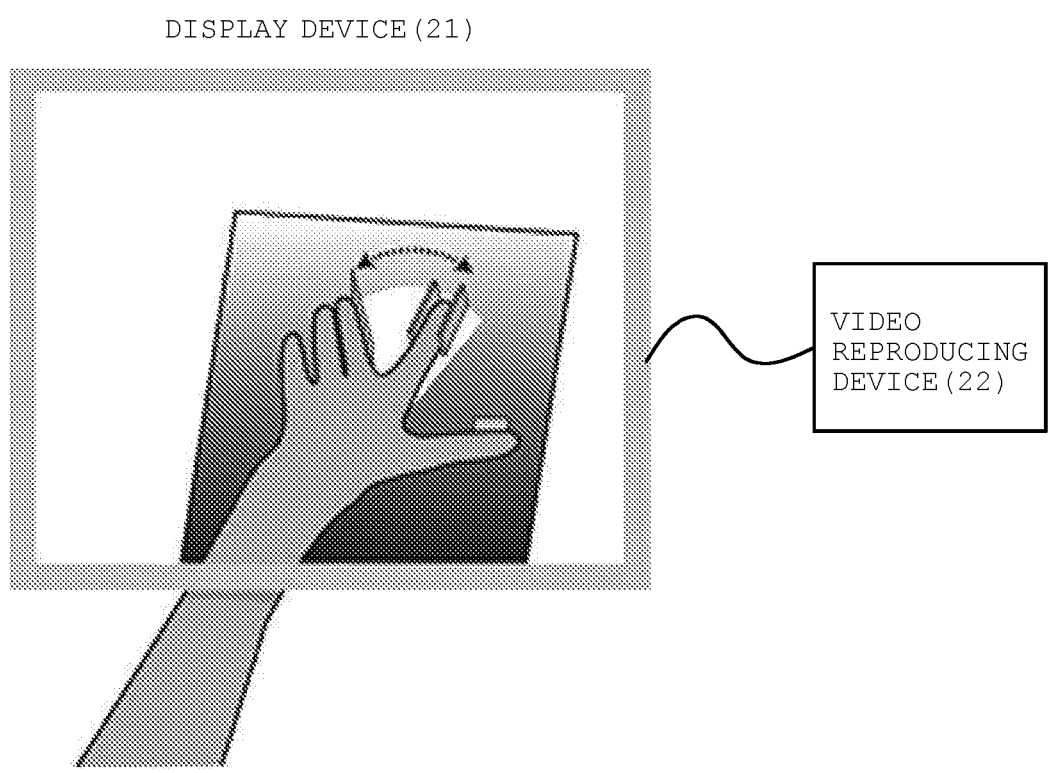

[FIG. 3]
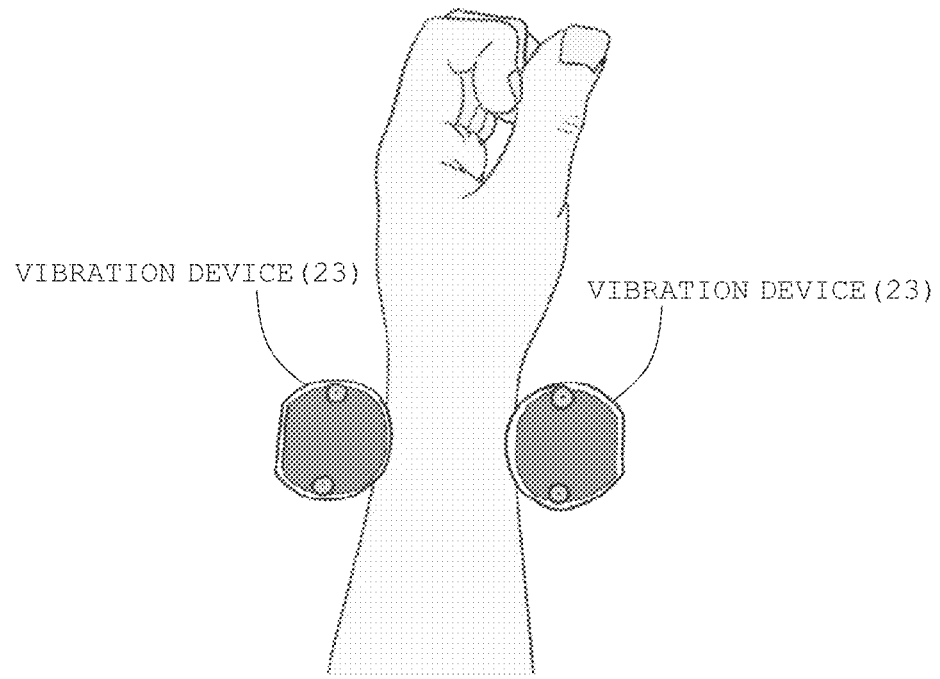

[FIG. 4]
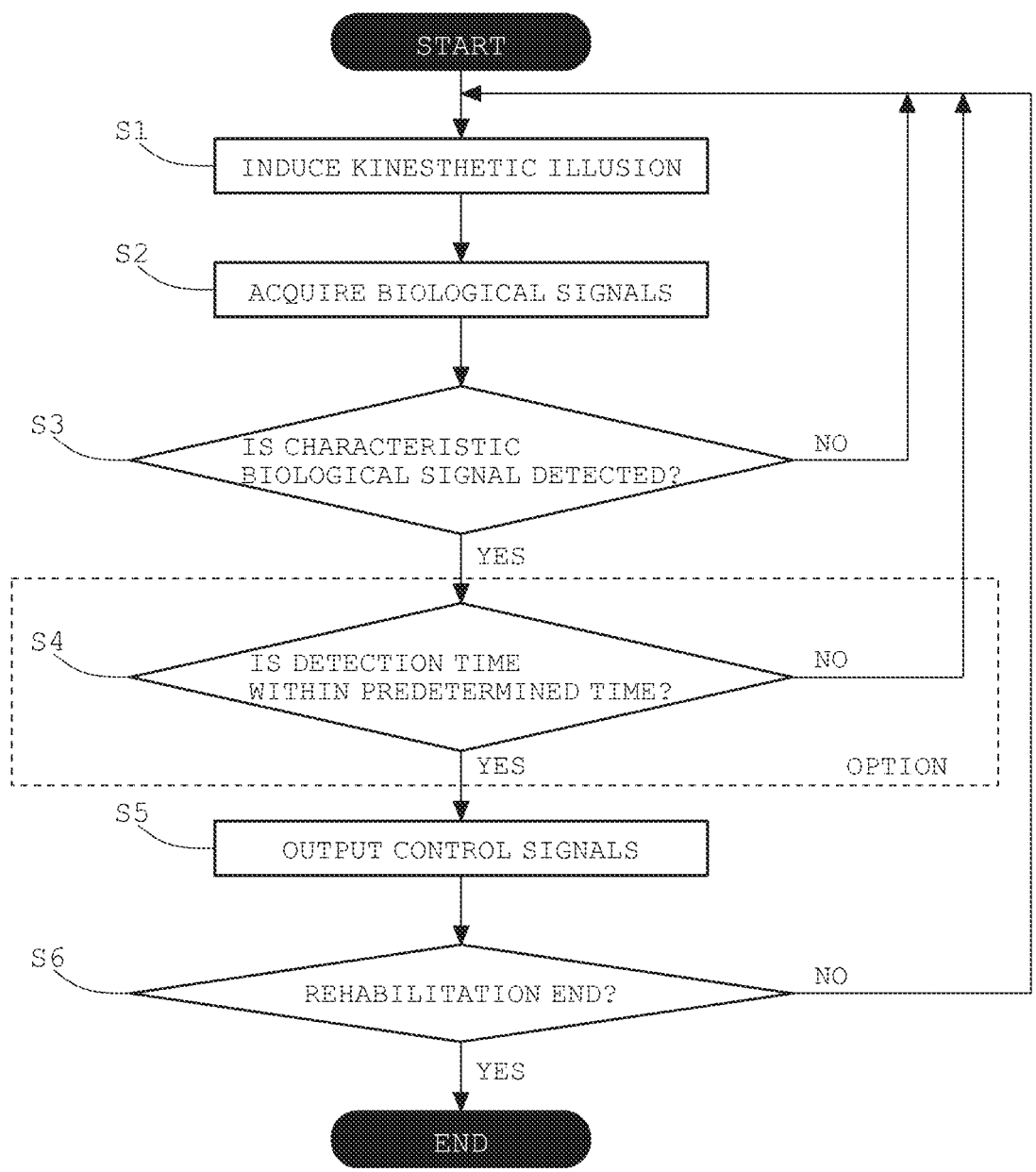

[FIG. 5]
(a) ILLUSION CONDITION 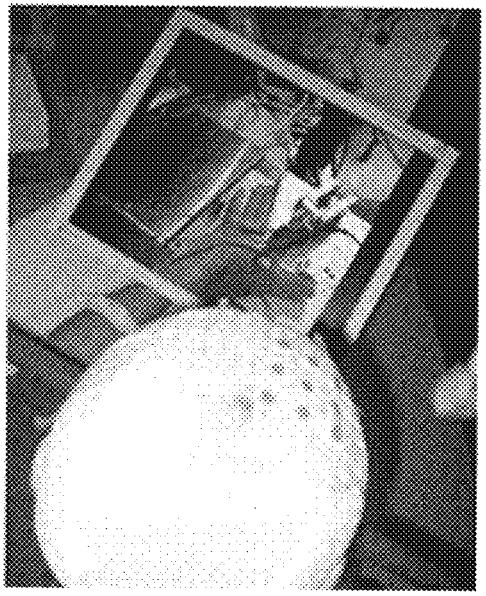 (b) NON-ILLUSION CONDITION 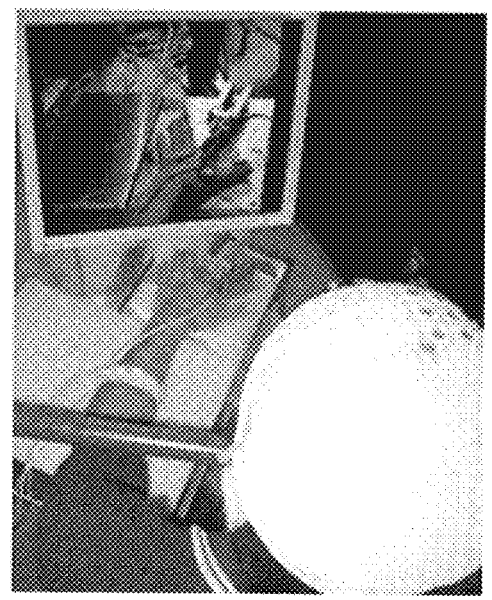

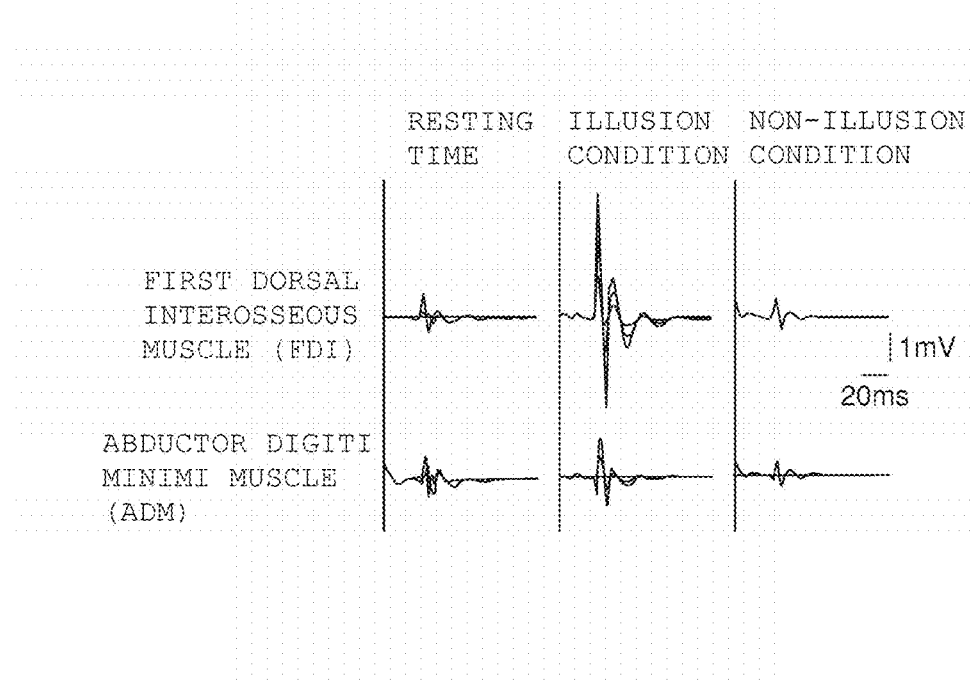

[FIG. 7]
(a) NON-ILLUSION CONDITION
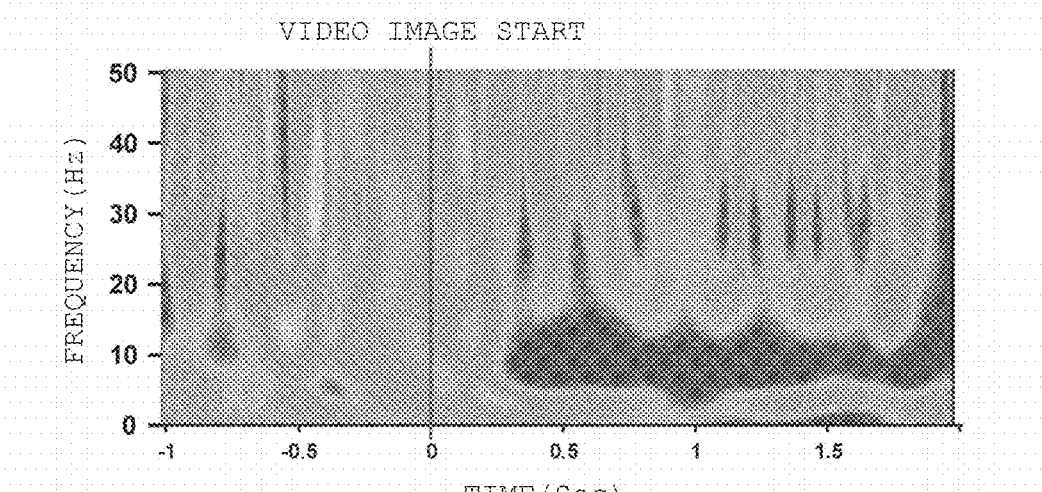
(b) ILLUSION CONDITION
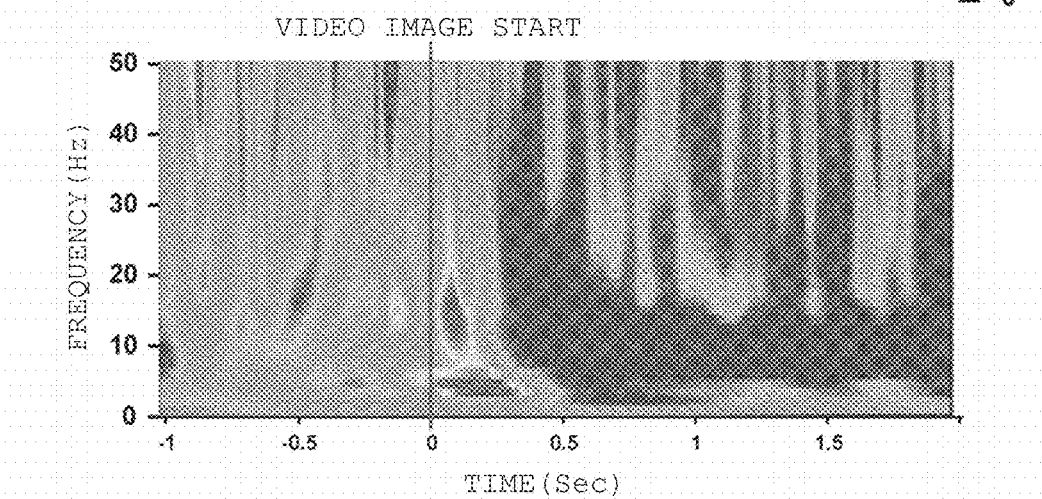

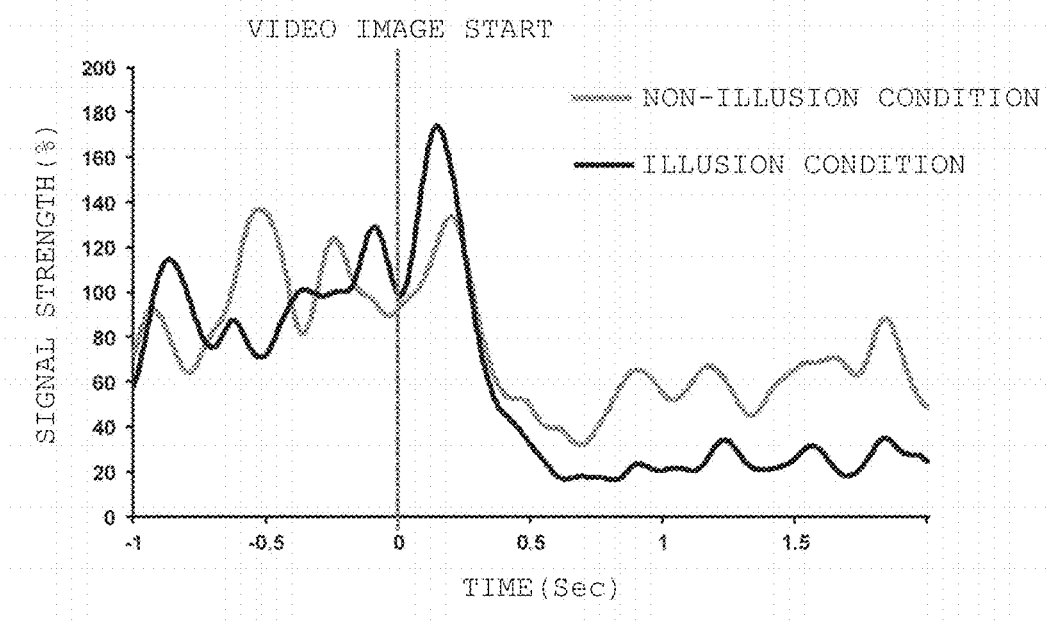
[FIG. 8]

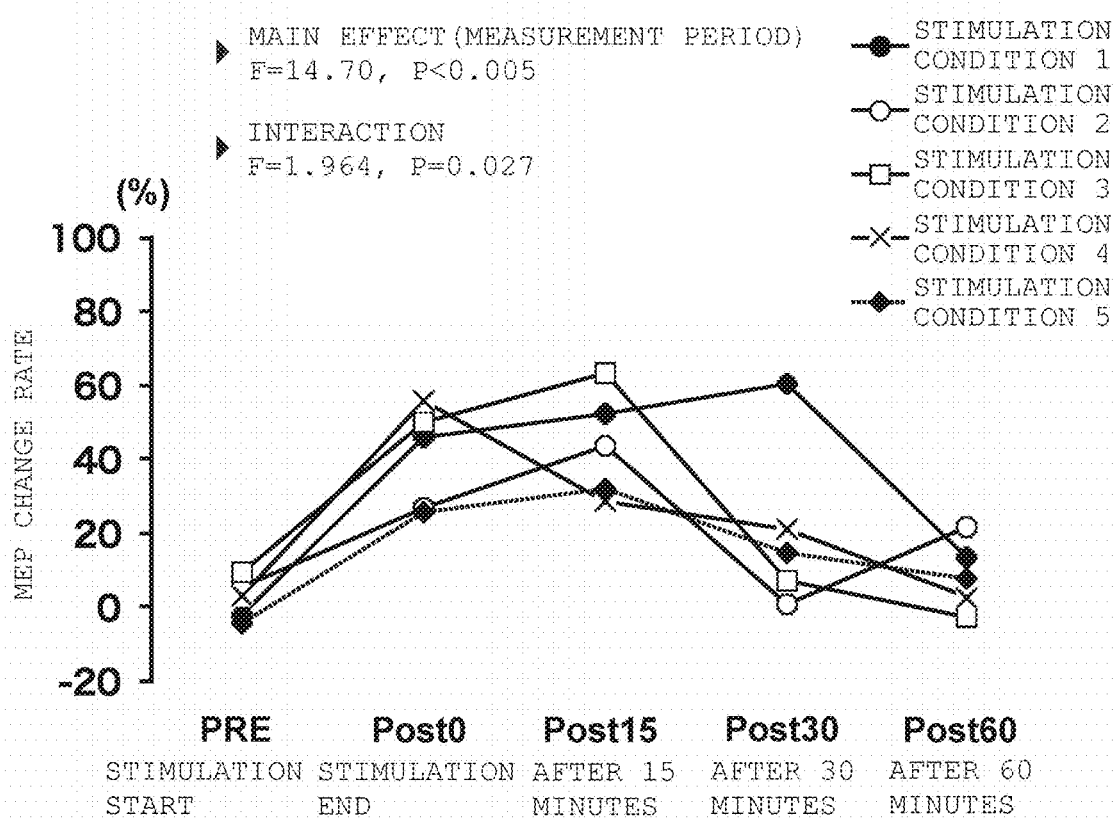

[FIG. 10]
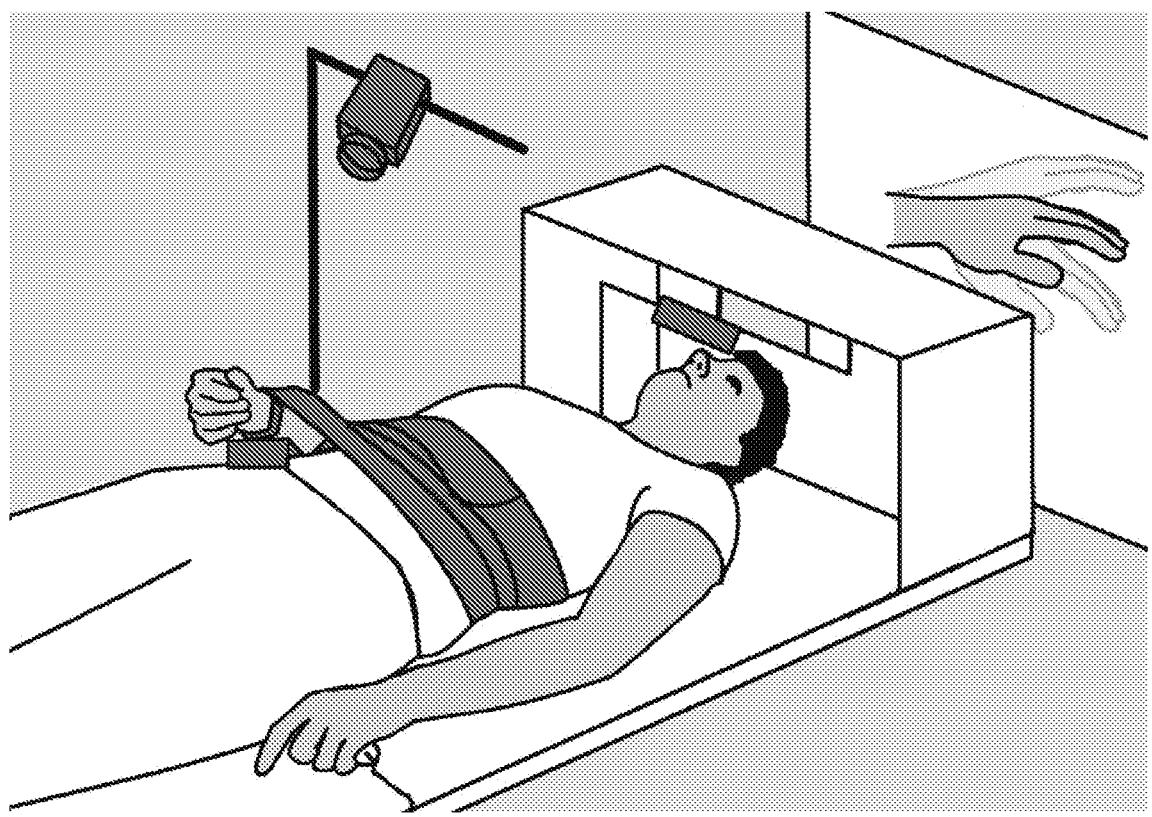

[FIG. 11]
(a)
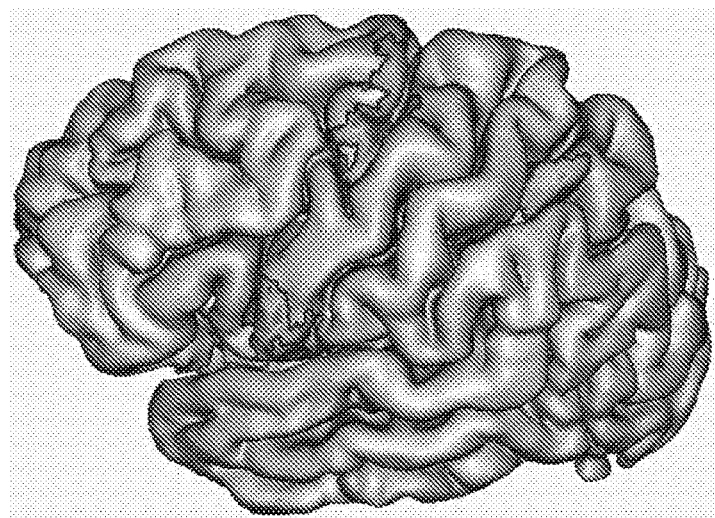
(b)
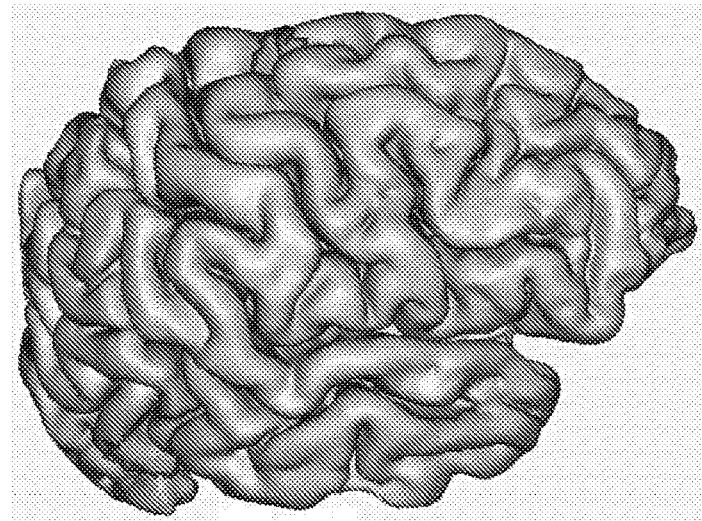
(c)
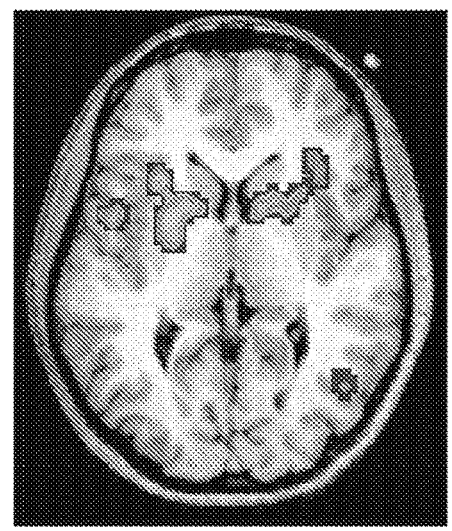

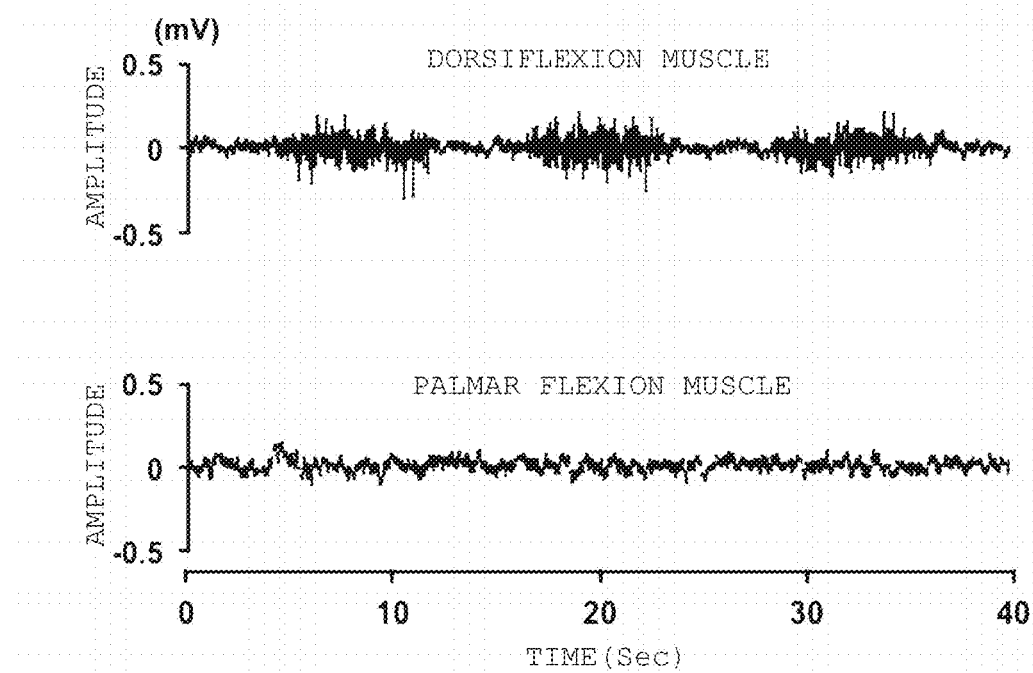
[FIG. 12]

[FIG. 13]
(a)
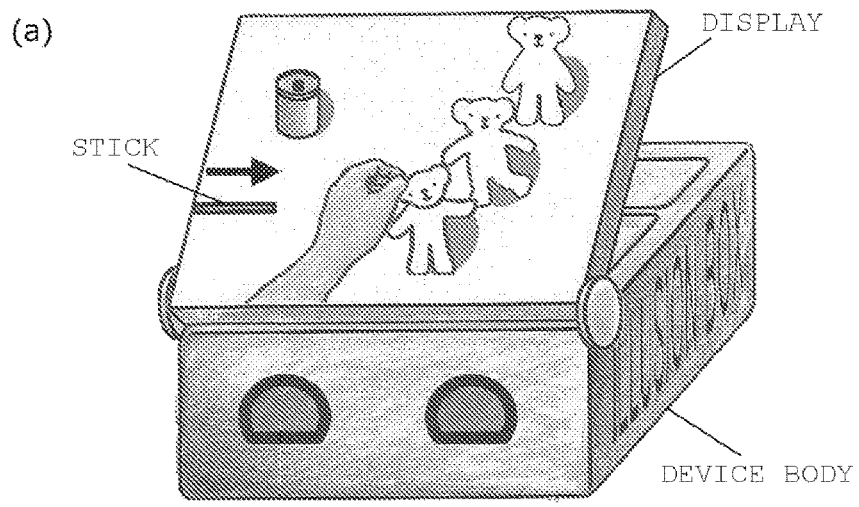
(b)
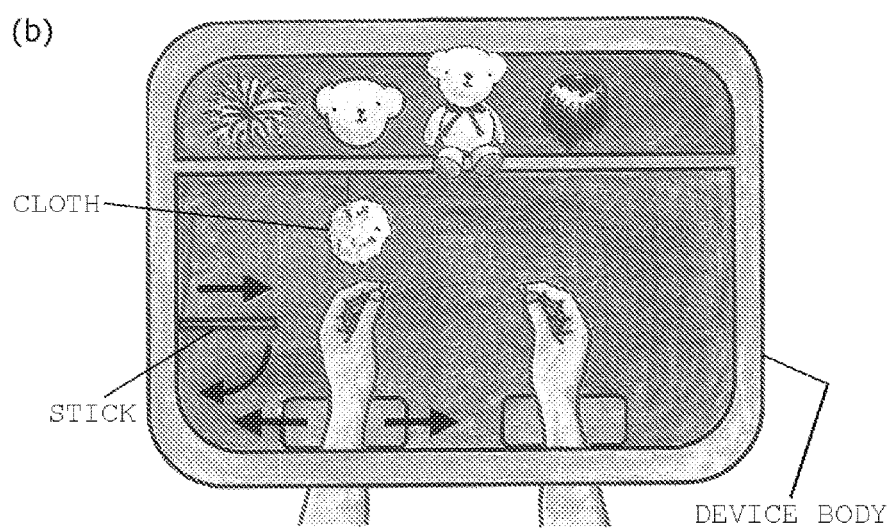
(c)
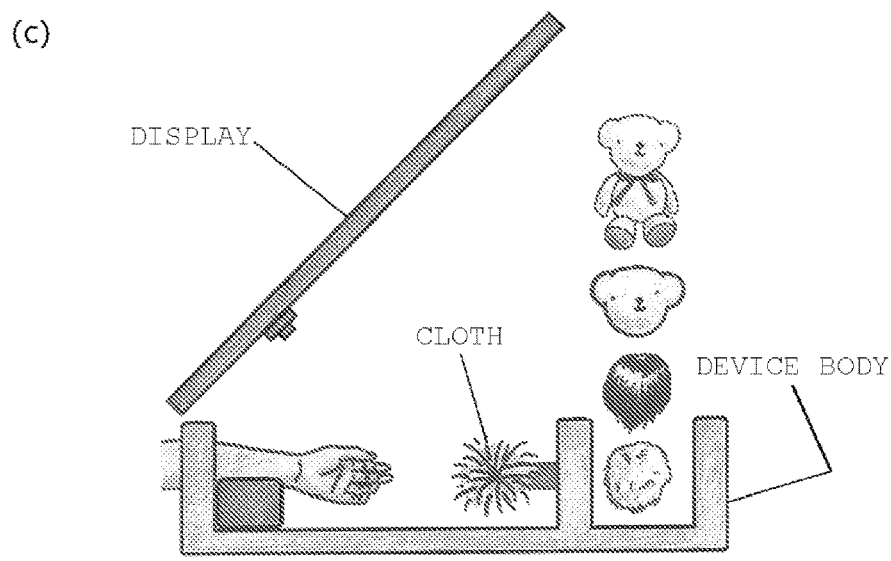

DEVICE FOR REHABILITATION, REHABILITATION SYSTEM PROVIDED THEREWITH, PROGRAM FOR REHABILITATION AND REHABILITATION METHOD

TECHNICAL FIELD

The present invention relates to a device for rehabilitation for performing rehabilitation for recovering a motor function of a patient who has difficulty in or is incapable of voluntary movements by his/her intention like a patient with hemiplegia after a stroke, a rehabilitation system including the device, a program for rehabilitation, and a rehabilitation method.

BACKGROUND ART

Conventionally, as a technology for performing rehabilitation to a patient, for example, Japanese Patent No. 4618795 proposes a rehabilitation device including a visual stimulation device which shows a normal movement of a paralyzed body part to a patient, a body driving device, means for detecting a biological signal of the patient, means for generating data for driving the body from the detected biological signal, and means for transmitting the generated data to the body driving device, and is programmed so that the body driving device forcedly starts the same movement as the movement of the body part shown to the patient in cooperation with the visual stimulation device with the detection of the biological signal or an external signal as a trigger and continues the movement for a fixed period of time (Patent Literature 1).

CITATION LIST

Patent Literature

Patent Literature 1: Japanese Patent No. 4618795

SUMMARY OF INVENTION

Technical Problem

However, in a patient with hemiplegia after a stroke or the like, it is known that there is abnormal inhibitory input from a non-damaged hemisphere to a motor area of a damaged hemisphere (so-called abnormal interhemisphere inhibition), and it is considered that it is made difficult to generate an intention to move by himself/herself due to the abnormal interhemisphere inhibition. Therefore, as described in the Patent Literature 1 above, there are many patients who are incapable of not only moving the body but also expressing an intention to voluntarily move the body, and in this case, there is a problem that the biological signal to be the trigger in Patent Literature 1 cannot be generated in the first place.

Also, in Patent Literature 1, it is described that, when the biological signal of the patient cannot be utilized as the trigger, an external signal (sound emitted at a predetermined interval) is utilized as the trigger. However, in the case of utilizing the external signal, the visual stimulation device and the body driving device are just operated completely regardless of the intention of the patient so that a rehabilitation effect cannot be actually expected.

The present invention is implemented in order to solve such a problem, and an object is to provide a device for rehabilitation capable of giving a patient who cannot express an intention to voluntarily move the body a kinesthetic illusion that his/her own body is moving and thus achieving a high rehabilitation effect, a rehabilitation system including it, a program for rehabilitation, and a rehabilitation method.

Solution to Problem

A device for rehabilitation relating to the present invention is a device for rehabilitation used in physical rehabilitation, and includes: a biological signal acquisition unit that acquires biological signals from a patient imparted with predetermined illusory stimulation for inducing a kinesthetic illusion that his/her own rehabilitation target part is moving; a characteristic biological signal detection unit that analyzes the biological signals and detects a characteristic biological signal indicating a state where the kinesthetic illusion is induced; and a control signal output unit that outputs control signals for controlling body driving means that forcedly moves the rehabilitation target part and/or brain simulating means that stimulates the brain, when the characteristic biological signal is detected by the characteristic biological signal detection unit.

In addition, as one aspect of the present invention, the illusory stimulation may be visual stimulation by displaying a video image that a virtual part simulating the rehabilitation target part performs a predetermined movement at a position overlapping with the rehabilitation target part and showing the video image to the patient.

Further, as one aspect of the present invention, the illusory stimulation may be sensory stimulation by vibrating the rehabilitation target part or stimulating skin of the rehabilitation target part.

In addition, as one aspect of the present invention, the device for rehabilitation may include body self-owning feeling inducing means that imparts stimulation for inducing a body self-owning feeling that his/her own body is his/her own before inducing the kinesthetic illusion by the illusory stimulation.

Further, as one aspect of the present invention, the control signal output unit may output the control signals when the characteristic biological signal is detected within a predetermined time after the illusory stimulation is imparted.

Also, as one aspect of the present invention, the control signal output unit may output control signals for controlling virtual part driving means that drives the virtual part simulating the rehabilitation target part, instead of the control signals to the body driving means and/or the brain stimulating means, or together with the control signals to the body driving means and/or the brain stimulating means, when the characteristic biological signal is detected by the characteristic biological signal detection unit.

In addition, a rehabilitation system relating to the present invention includes the device for rehabilitation according to any one of claim 1 to claim 6, kinesthetic illusion inducing means that induces the kinesthetic illusion, and the body driving means and/or the brain stimulating means.

Further, a program for rehabilitation relating to the present invention is a program for rehabilitation used in physical rehabilitation, and makes a computer function as: a biological signal acquisition unit that acquires biological signals from a patient imparted with predetermined illusory stimulation for inducing a kinesthetic illusion that his/her own rehabilitation target part is moving; a characteristic biological signal detection unit that analyzes the biological signals and detects a characteristic biological signal indicating a state where the kinesthetic illusion is induced; and a control signal output unit that outputs control signals for controlling body driving means that forcedly moves the rehabilitation target part and/or brain simulating means that stimulates the brain, when the characteristic biological signal is detected by the characteristic biological signal detection unit.

In addition, a rehabilitation method relating to the present invention is a rehabilitation method used in physical rehabilitation, and includes: a biological signal acquisition step of acquiring biological signals from a patient imparted with predetermined illusory stimulation for inducing a kinesthetic illusion that his/her own rehabilitation target part is moving; a characteristic biological signal detection step of analyzing the biological signals and detecting a characteristic biological signal indicating a state where the kinesthetic illusion is induced; and a control signal output step of outputting control signals for controlling body driving means that forcedly moves the rehabilitation target part and/or brain simulating means that stimulates the brain, when the characteristic biological signal is detected by the characteristic biological signal detection unit.

Advantageous Effects of Invention

According to the present invention, even to a patient who cannot express an intention to voluntarily move the body, a kinesthetic illusion that his/her own body is moving is induced, and a high rehabilitation effect can be obtained.

BRIEF DESCRIPTION OF DRAWINGS

FIG. 1 is a block diagram illustrating one embodiment of a rehabilitation system including a device for rehabilitation relating to the present invention.

FIG. 2 is a diagram illustrating one example of kinesthetic illusion inducing means that imparts visual stimulation in the present embodiment.

FIG. 3 is a diagram illustrating one example of kinesthetic illusion inducing means that imparts sensory stimulation in the present embodiment.

FIG. 4 is a flowchart diagram illustrating a rehabilitation method using the rehabilitation system of the present embodiment.

FIG. 5(a) is a photograph illustrating a situation of an illusion condition and FIG. 5(b) is a photograph illustrating a situation of a non-illusion condition, in an example 1.

FIG. 6 is a graph illustrating a superimposed waveform of a motor evoked potential recorded under individual conditions in the example 1.

FIG. 7 are graphs illustrating signal strength of individual frequency components in (a) the non-illusion condition and (b) the illusion condition, in an example 2.

FIG. 8 is a graph illustrating a time change of an average value of the signal strength in a frequency band of 8 to 13 Hz, in the example 2.

FIG. 9 is a graph illustrating a time change of an average value of change rates of the motor evoked potential under individual stimulation conditions in an example 3.

FIG. 10 is an image diagram illustrating an experimental condition of an example 4.

FIG. 11 are fMRI images of the brain illustrating brain activity in a state of perceiving a kinesthetic illusion in the example 4, and FIG. 11(a) is a left side view, FIG. 11(b) is a right side view, and FIG. 11(c) is a sectional view.

FIG. 12 is a graph illustrating an electromyogram of a dorsiflexion muscle and a palmar flexion muscle, in an example 5.

FIG. 13(a) is a perspective view, FIG. 13(b) is a plan view in which a display part is omitted, and FIG. 13(c) is a right side sectional view illustrating an experimental device in an example 6.

DESCRIPTION OF EMBODIMENTS

The inventor of the present application has found that, as a result of intensive study, even in a state where the patient is not actually moving and is resting, by imparting predetermined stimulation, the patient can be made to perceive a feeling as if his/her own body (rehabilitation target part) is moving. In the present invention, perception of the moving feeling contrary to reality as described above is referred to as a kinesthetic illusion.

The inventor of the present application has found that, as a result of intensive study, when the kinesthetic illusion is induced, an activity close to a brain activity assumed to be needed when actually executing a movement is obtained. Therefore, it is predicted that, by using the kinesthetic illusion, a motor area of the brain is activated and the abnormal interhemisphere inhibition is improved. In addition, it is presumed that an expression of a voluntary movement is urged by improvement of the abnormal interhemisphere inhibition and it is effective for recovering a motor function of a patient with hemiplegia or the like, and the present invention is completed.

Hereinafter, one embodiment of a device for rehabilitation, a rehabilitation system including it, a program for rehabilitation and a rehabilitation method relating to the present invention will be described using drawings.

As illustrated in FIG. 1, a rehabilitation system 1 of the present embodiment mainly includes kinesthetic illusion inducing means 2, biological signal sampling means 3, body driving means 4, brain stimulating means 5, virtual part driving means 8, and a device 10 for rehabilitation of the present embodiment. Hereinafter, individual configurations will be described.

The kinesthetic illusion inducing means 2 induces the kinesthetic illusion that his/her own body (rehabilitation target part) is moving by imparting predetermined illusory stimulation to a patient. In the present embodiment, as the illusory stimulation to be imparted by the kinesthetic illusion inducing means 2, there are mainly visual stimulation and sensory stimulation.

In the case of imparting the visual stimulation as the illusory stimulation, the kinesthetic illusion inducing means 2 is, as illustrated in FIG. 2, configured by a display device 21 such as a liquid crystal display or a head-mounted display and a video reproducing device 22 such as a personal computer that inputs a video image for the visual stimulation to the display device 21 or the like. In addition, a tablet type portable terminal for which the display device 21 and the video reproducing device 22 are integrally configured or the like can be also utilized. Also, as the video image for the visual stimulation, a video image in which a virtual part simulating the rehabilitation target part is performing a predetermined movement is used.

Then, as illustrated in FIG. 2, by displaying the virtual part at a position overlapping with the rehabilitation target part of the patient and showing the virtual part to the patient, a feeling that his/her own body is truly his/her own (so-called body self-owning feeling) is induced, and the kinesthetic illusion is induced to the patient by displaying the video image for the visual stimulation in the overlapping state. Note that it is preferable to make the rehabilitation target part of the patient himself/herself into a video image for the video image for the visual stimulation, however, it is not limited thereto, and it may be a video image of another person or a video image of computer graphics or the like as long as it simulates a color and a shape or the like similar to that of the rehabilitation target part of the patient. In addition, the video reproducing device 22 may be shared by the device 10 for rehabilitation, and may be separate from the device 10 for rehabilitation.

In the case of imparting the sensory stimulation as the illusory stimulation, the kinesthetic illusion inducing means 2 is configured by a vibration device 23 such as a vibrator. Then, in the case where the rehabilitation target part is a wrist for example, as illustrated in FIG. 3, by vibrating the vibration device 23 in a state of applying it to a tendon of the wrist, a muscular spindle ignites and the kinesthetic illusion is induced.

In addition, the kinesthetic illusion inducing means 2 may impart the sensory stimulation by stimulating skin of the rehabilitation target part, and induce the kinesthetic illusion. Specifically, it can be considered to stick a wire near the rehabilitation target part with a tape and stretch the skin by pulling the wire. Or, the sensory stimulation can be imparted also by mounting a palm on a rotatable disk and rotating the disk in a predetermined direction.

The biological signal sampling means 3 samples biological signals indicating a brain activity such as a brain wave signal or a cerebral blood flow, or a muscular activity such as an action potential of muscles or a movement of a joint or the like. In the present embodiment, the biological signal sampling means 3 that samples the brain wave signals is configured by an electrode which is arranged on a scalp and captures a potential change generated accompanying the brain activity, and an electroencephalograph which frequency-analyzes the brain wave signal sampled at the electrode and outputs it as signal strength data for each frequency component or the like. In addition, as the biological signal sampling means 3 that samples the cerebral blood flow, a near infrared spectroscopic blood flow meter or the like is used.

In addition, as the biological signal sampling means 3 that samples the action potential of the muscles, an electromyograph or the like is used. The electromyograph measures the action potential of the muscles related to the movement of the rehabilitation target part, also frequency-analyzes the action potential signal and outputs it as the signal strength data for each frequency component. Further, as the biological signal sampling means 3 that samples the movement of the joint, an acceleration and an angle when the joint is moved may be calculated by image processing from a motion capture other than an acceleration sensor and an angle sensor.

The body driving means 4 forcedly moves the body (rehabilitation target part) of the patient to exercise. In the present embodiment, for the body driving means 4, a case of mechanically moving the body of the patient and a case of electrically moving the body of the patient are exemplified. Examples of the mechanical body driving means 4 include a power assisting device that is mounted on the rehabilitation target part and driven by an actuator or the like to forcedly move the body. On the other hand, examples of the electrical body driving means 4 include an electrical stimulus device that contracts the muscles by making a low frequency pulse current flow to the electrode stuck to the rehabilitation target part and forcedly moves the body.

The brain stimulating means 5 induces plasticity of the brain by non-invasively stimulating the brain of the patient. In the present embodiment, examples of a method of stimulating the brain by the brain stimulating means 5 include transcranial magnetic stimulation (TMS) and transcranial direct current stimulation (tDCS).

The transcranial magnetic stimulation is a method of inducing a magnetic field right below a stimulation coil by making a quick pulse current flow to the stimulation coil and inducing an eddy current inside the brain through electromagnetic induction. By installing the stimulation coil on a primary motor area (M1), cortical cells that run in parallel are stimulated, and pyramidal tract cells are excited through some synapses. In such a manner, since the transcranial magnetic stimulation can non-invasively stimulate the cerebral cortex and an interhemisphere circuit, therapeutic intervention effect is expected.

In addition, the transcranial direct current stimulation is a non-invasive stimulation method with less pain similarly to the transcranial magnetic stimulation. Specifically, in the case of stimulating the primary motor area, one of a pair of stimulation electrodes is arranged right above the primary motor area, the other is arranged on the eye socket on an opposite side, and excitability of a stimulation part is increased or lowered by stimulation time and polarity. The transcranial magnetic stimulation and the transcranial direct current stimulation both perform adjustment to increase the excitability in the primary motor area on a damaged hemisphere side or to lower the excitability in the primary motor area on a normal hemisphere side. Therefore, it is conceivable that it leads to the improvement of the motor function of a patient with a stroke or the like.

Note that, as described above, a composite muscular activity potential recorded from a target muscle by stimulating the primary motor area of the brain is referred to as a motor evoked potential (MEP). In addition, in the present embodiment, in order to induce a strong kinesthetic illusion to the patient, the kinesthetic illusion inducing means 2 imparts both of the visual stimulation and the sensory stimulation at the same timing. However, without being limited to this configuration, the sufficient kinesthetic illusion can be induced just by either one of the visual stimulation and the sensory stimulation.

The virtual part driving means 8 drives a virtual part simulating the rehabilitation target part of the patient capable of expressing an intention to voluntarily move the body even slightly. In the present embodiment, the virtual part driving means 8 has a configuration equal to the kinesthetic illusion inducing means 2 in the case of imparting the visual stimulation, and is configured by the display device 21 such as a liquid crystal display or a head-mounted display and the video reproducing device 22 such as a personal computer that makes the display device 21 display the virtual part.

However, in the kinesthetic illusion inducing means 2, as described above, the video image for the visual stimulation in which the virtual part is performing a predetermined movement regardless of the intention of the patient is used. In contrast, in the virtual part driving means 8, as described later, feedback control can be performed so that the virtual part moves in accordance with timing at which the patient originates the intention to voluntarily move the body. In this case, similarly to the case of inducing the kinesthetic illusion, it is needed to display the virtual part at a position overlapping with the rehabilitation target part of the patient and show the virtual part to the patient.

Note that, as a method of controlling an operation of the virtual part, an image processing program of trimming the rehabilitation target part from a still image of the patient and moving the trimming area as the virtual part is conceivable.

Or, an image processing program of producing computer graphics simulating the rehabilitation target part of the patient and moving the virtual part by the computer graphics may be used.

The device 10 for rehabilitation is a device used in physical rehabilitation together with each means described above. In the present embodiment, the device 10 for rehabilitation is configured by a computer such as a personal computer, and as illustrated in FIG. 1, mainly includes storage means 6 and arithmetic processing means 7.

The storage means 6 stores various kinds of data, and functions as a working area when the arithmetic processing means 7 performs arithmetic processing. In the present embodiment, the storage means 6 is configured by a ROM (Read Only Memory), a RAM (Random Access Memory) and a flash memory or the like, and as illustrated in FIG. 1, includes a program storage unit 61, a detection target frequency storage unit 62, a threshold-for-determination storage unit 63, and a stimulation timing storage unit 64. Hereinafter, individual configuration units will be described in more detail.

In the program storage unit 61, a program 1a for rehabilitation in the present embodiment is installed. Then, by the execution of the program 1a for rehabilitation by the arithmetic processing means 7, the computer as the device 10 for rehabilitation is made to function as the individual configuration units described later.

Note that a utilization form of the program 1a for rehabilitation is not limited to the above-described configuration. For example, the program 1a for rehabilitation may be stored in a computer-readable recording medium such as a CD-ROM or a DVD-ROM, and may be directly read from the recording medium and executed. In addition, the storage means 6 may be provided in a data server or the like installed separate from the device 10 for rehabilitation and the program may be utilized by an ASP (Application Service Provider) method or a cloud computing method from the data server or the like.

The detection target frequency storage unit 62 stores a detection target frequency which is a frequency component to be used when a characteristic biological signal detection unit 72 described later detects a characteristic biological signal. In the present invention, the characteristic biological signal is a concept including all the brain activities (the brain wave and the cerebral blood flow) and the muscular activities (the action potential of the muscles and the acceleration and angle of the joint) indicating the state where the kinesthetic illusion is induced.

As described above, in the present embodiment, in the case of sampling the brain activity as the biological signal, the biological signal sampling means 3 outputs the brain wave signal as the signal strength for each frequency component. In the meantime, as described later in an example 2, the inventor of the present application has found that, when the kinesthetic illusion is induced, the signal strength in a predetermined frequency component largely changes. Then, in the present embodiment, an appropriate detection target frequency is set, and the large change in the signal strength of the frequency component is detected as a characteristic brain activity.

Note that, in the present embodiment, 8 to 13 Hz corresponding to alpha waves is stored as the detection target frequency, however, it may be appropriately set as long as it is the frequency band in which the characteristic brain activity can be detected. For example, it may be the single frequency component (example: 10 Hz), may be the plurality of frequency components (example: 5 Hz and 10 Hz), or may be the plurality of frequency bands (example: 3 to 5 Hz and 8 to 13 Hz).

In addition, as described above, in the case of sampling the action potential of the muscles as the biological signal, the biological signal sampling means 3 outputs the action potential as the signal strength for each frequency component. Therefore, in the detection target frequency storage unit 62, the detection target frequency which is the frequency component used when detecting the characteristic muscle action potential is stored.

The threshold-for-determination storage unit 63 stores a threshold for determination for the characteristic biological signal detection unit 72 described later to determine whether or not it is the characteristic biological signal. In the present embodiment, in the case of sampling the brain activity as the biological signal, the large change in the signal strength of the detection target frequency of the brain wave signal, or the large change in the cerebral blood flow is detected as the characteristic brain activity (biological signal). Therefore, the large change in the signal strength of the brain wave signal or the large change in the cerebral blood flow at what degree is to be determined as the characteristic brain activity is determined by the threshold for determination.

In addition, in the present embodiment, in the case of sampling the muscular activity as the biological signal, the large change in the signal strength of the detection target frequency of the muscle action potential, or the large change in the acceleration or angle of the joint is detected as the characteristic muscular activity (biological signal). Therefore, the large change in the signal strength of the action potential or the large change in the movement of the joint at what degree is to be determined as the characteristic muscular activity is determined by the threshold for determination.

Note that, in the present embodiment, in order to set an appropriate threshold for determination for each patient, a value for which a double of a standard deviation (2SD) is added to an average value of the signal strength during resting before imparting the illusory stimulation is set as the threshold for determination. However, it is not limited thereto, and the threshold for determination may be fixed at a fixed value.

The stimulation timing storage unit 64 stores stimulation timing of imparting the illusory stimulation for inducing the kinesthetic illusion. The stimulation timing is, as described later, data for guaranteeing that the characteristic biological signal detected by the characteristic biological signal detection unit 72 is due to induction of the kinesthetic illusion.

Specifically, the stimulation timing is the data that can be utilized in the case where the kinesthetic illusion inducing means 2 imparts the visual stimulation. That is, a timing chart indicating timing at which the virtual part simulating the rehabilitation target part performs the predetermined movement in the video image for the visual stimulation on a time base is stored as the stimulation timing in the stimulation timing storage unit 64.

Next, the arithmetic processing means 7 exchanges various kinds signals with each means described above, and executes various kinds of arithmetic processing. In the present embodiment, the arithmetic processing means 7 is configured by a CPU (Central Processing Unit) or the like, and by executing the program 1a for rehabilitation installed in the storage means 6, as illustrated in FIG. 1, functions as a biological signal acquisition unit 71, the characteristic biological signal detection unit 72, and a control signal output unit 73. Hereinafter, individual configuration units will be described in more detail.

The biological signal acquisition unit 71 acquires the biological signals from the patient imparted with the predetermined illusory stimulation for inducing the kinesthetic illusion. In the present embodiment, when sampling the biological signals from the patient, the kinesthetic illusion that his/her own body is moving is induced. Specifically, the biological signal acquisition unit 71 acquires the biological signals from the biological signal sampling means 3 while imparting the predetermined illusory stimulation by the kinesthetic illusion inducing means 2.

Note that, in the present embodiment, in the case where the biological signal sampling means 3 is the electroencephalograph, the biological signal acquisition unit 71 acquires signal strength data for each frequency component obtained from the brain wave signal as the biological signals. Also, in the case where the biological signal sampling means 3 is the near infrared spectroscopic blood flow meter, the biological signal acquisition unit 71 acquires the data of the cerebral blood flow as the biological signals. Further, in the case where the biological signal sampling means 3 is the electromyograph, the biological signal acquisition unit 71 acquires the signal strength data for each frequency component obtained from the action potential signal of the muscles as the biological signals. In addition, in the case where the biological signal sampling means 3 is the acceleration sensor and the angle sensor, the biological signal acquisition unit 71 acquires the acceleration data and angle data of the joint as the biological signals.

The characteristic biological signal detection unit 72 analyzes the biological signals sampled from the patient in real time, and detects the characteristic biological signal. In the present embodiment, in the case of detecting the characteristic brain activity from the brain wave signals, the characteristic biological signal detection unit 72 analyzes the signal strength data for each frequency component relating to the brain wave signals acquired by the biological signal acquisition unit 71.

Specifically, the characteristic biological signal detection unit 72 refers to the detection target frequency stored in the detection target frequency storage unit 62, and time-sequentially extracts the signal strength of the detection target frequency. Then, the characteristic biological signal detection unit 72 compares the extracted signal strength with the threshold for determination stored in the threshold-for-determination storage unit 63, and monitors whether or not there is the large change. As a result, when the signal strength exceeds the threshold for determination, or when the signal strength becomes equal to or lower than the threshold for determination, detection is performed as the characteristic brain activity (biological signal).

In addition, in the present embodiment, in the case of detecting the characteristic brain activity from the cerebral blood flow, the characteristic biological signal detection unit 72 analyzes the cerebral blood flow acquired by the biological signal acquisition unit 71. Specifically, the characteristic biological signal detection unit 72 compares the cerebral blood flow with the threshold for determination stored in the threshold-for-determination storage unit 63, and monitors whether or not there is the large change. As a result, when the cerebral blood flow exceeds the threshold for determination, or when the cerebral blood flow becomes equal to or lower than the threshold for determination, detection is performed as the characteristic brain activity (biological signal).

Further, in the present embodiment, in the case of detecting the characteristic muscular activity from the action potential of the muscles, the characteristic biological signal detection unit 72 analyzes the signal strength data for each frequency component relating to the action potential signals acquired by the biological signal acquisition unit 71. Specifically, the characteristic biological signal detection unit 72 refers to the detection target frequency stored in the detection target frequency storage unit 62, and time-sequentially extracts the signal strength of the detection target frequency. Then, the characteristic biological signal detection unit 72 compares the extracted signal strength with the threshold for determination stored in the threshold-for-determination storage unit 63, and monitors whether or not there is the large change. As a result, when the signal strength exceeds the threshold for determination, or when the signal strength becomes equal to or lower than the threshold for determination, detection is performed as the characteristic muscular activity (biological signal).

In addition, in the present embodiment, in the case of detecting the characteristic muscular activity from the movement of the joint, the characteristic biological signal detection unit 72 analyzes the acceleration data and the angle data acquired by the biological signal acquisition unit 71. Specifically, the characteristic biological signal detection unit 72 compares the acceleration data and the angle data with the threshold for determination stored in the threshold-for-determination storage unit 63, and monitors whether or not there is the large change. As a result, when the acceleration data and the angle data exceed the threshold for determination, or when the acceleration data and the angle data become equal to or lower than the threshold for determination, detection is performed as the characteristic muscular activity (biological signal).

The control signal output unit 73 outputs control signals for controlling the body driving means 4 and/or the brain stimulating means 5 when the characteristic biological signal is detected. In the present embodiment, the control signal output unit 73 monitors whether or not the characteristic biological signal detection unit 72 detects the characteristic biological signal at all times. Then, at the timing of detecting the characteristic biological signal, the control signals that control the body driving means 4 and/or the control signals that control the brain stimulating means 5 are outputted.

Specifically, examples of the control signals that control the body driving means 4 include the control signal that drives the power assisting device and the control signal that makes the electrical stimulus device output a pulse current. In addition, the examples of the control signals that control the brain stimulating means 5 include the control signal that drives a device relating to the transcranial magnetic stimulation and the transcranial direct current stimulation.

In addition, in the present embodiment, the control signal output unit 73 has an option function for guaranteeing that the characteristic biological signal detected by the characteristic biological signal detection unit 72 is due to the induction of the kinesthetic illusion. That is, the control signal output unit 73 outputs the control signals when the characteristic biological signal is detected within a predetermined time after the illusory stimulation is imparted by the kinesthetic illusion inducing means 2.

Specifically, the kinesthetic illusion inducing means 2 that imparts the visual stimulation includes, as described above, the display device 21 and the video reproducing device 22. Therefore, the control signal output unit 73 acquires the time at which reproduction of the video image for the visual stimulation is started from the video reproducing device 22, also refers to the stimulation timing stored in the stimulation timing storage unit 64, and recognizes the stimulation imparting time to impart the visual stimulation to the patient.

Then, every time the characteristic biological signal detection unit 72 detects the characteristic biological signal, the control signal output unit 73 determines whether or not the detection time is within the predetermined time after the stimulation imparting time. As a result, only in the case where it is within the predetermined time, the control signals are outputted. Note that, it is desirable to set the predetermined time to be within 1 to 2 seconds.

Note that, in the present embodiment, in order to improve the rehabilitation effect to the maximum, the control signal output unit 73 synchronously outputs the control signals to both of the body driving means 4 and the brain stimulating means 5. However, it is not limited to this configuration, and the control signals may be outputted to only one of the body driving means 4 and the brain stimulating means 5.

In addition, in the present embodiment, in the case where the patient capable of expressing an intention to voluntarily move the body even slightly is a target, the characteristic biological signal detection unit 72 detects the intention as the characteristic biological signal. Then, in accordance with the timing of the detection, the control signal output unit 73 outputs the control signals for controlling the virtual part driving means 8 instead of the control signals to the body driving means 4 and/or the brain stimulating means 5, or together with the control signals to the body driving means 4 and/or the brain stimulating means 5. Specifically, examples of the control signals that control the virtual part driving means 8 include an instruction signal that causes execution of image processing of moving the virtual part in the still image or the computer graphics by a moving amount according to a characteristic amount of the characteristic biological signal.

Next, effects by the device 10 for rehabilitation of the present embodiment, the rehabilitation system 1 including it, the program 1a for rehabilitation and the rehabilitation method will be explained using FIG. 4.

First, in the case of performing rehabilitation of the body (rehabilitation target part) to the patient with hemiplegia after a stroke or the like, the kinesthetic illusion inducing means 2, the biological signal sampling means 3, the body driving means 4, and the brain stimulating means 5 are mounted or set.

Next, using the kinesthetic illusion inducing means 2, the predetermined illusory stimulation is imparted to the patient and the kinesthetic illusion is induced (step S1). Thus, even in the state where the patient is resting, the feeling that his/her own body is truly his/her own (so-called body self-owning feeling), and the feeling that his/her own body is moving (kinesthetic illusion) are induced. In addition, in the case of imparting the visual stimulation as the illusory stimulation, by matching the colors and the shapes of the rehabilitation target part and the virtual part as much as possible and performing arrangement and display in such a way that there is no feeling of incompatibility with the rehabilitation target part of the patient himself/herself, the stronger body self-owning feeling and kinesthetic illusion are induced.

Subsequently, the biological signal acquisition unit 71 acquires the biological signals sampled from the patient to whom the kinesthetic illusion is induced (step S2). Thus, the signal strength for each frequency component is acquired from the brain wave signals and the action potential signals of the muscles in real time and time-sequentially. In addition, in the case of also using the data of the cerebral blood flow and the acceleration and the angle of the join, they are separately acquired.

Next, the characteristic biological signal detection unit 72 analyzes the biological signals sampled from the patient in real time, and detects the characteristic biological signal (step S3). At the time, in the present embodiment, in the case of using the brain waves and the action potential of the muscles as the biological signals, the detection target frequency for detecting the characteristic biological signal and the threshold for determination for determining whether or not it is the characteristic biological signal are appropriately set. Therefore, the characteristic brain activity and muscular activity corresponding to the kinesthetic illusion are highly accurately detected.

Unless the characteristic biological signal is detected (step S3: NO), the processing of steps S1 and S2 is repeated. On the other hand, every time the characteristic biological signal is detected (step S3: YES), the control signal output unit 73 determines whether or not the detection time is within the predetermined time after the stimulation imparting time (step S4).

As a result, when it is not within the predetermined time (step S4: NO), the control signal output unit 73 does not output the control signals and returns the processing to step S1. Thus, even in the case where the characteristic biological signal is detected, when it is the brain activity or the muscular activity not clearly due to the induction of the kinesthetic illusion, the control signals are not outputted. Therefore, it is not needed to operate the body driving means 4 and the brain stimulating means 5 in the state where the kinesthetic illusion is not induced, that is, in the state where the rehabilitation effect cannot be expected so much, and burdens on the patient are reduced.

On the other hand, in the case where it is within the predetermined time (step S4: YES), the control signal output unit 73 outputs the control signals (step S5). Thus, the body driving means 4 and the brain stimulating means 5 are synchronized with the timing at which the kinesthetic illusion is induced and are accurately driven. Therefore, the activity of the motor area is improved, and the above-described abnormal interhemisphere inhibition is improved. In addition, the expression of the voluntary movement is urged by the improvement of the abnormal interhemisphere inhibition, and the motor function of the patient with hemiplegia or the like is recovered.

Note that, after the control signals are outputted, the processing from step S1 is repeated until the rehabilitation ends (step S6).

Note that, in the present embodiment, the rehabilitation to the patient incapable of expressing an intention to voluntarily move the body like the patient with hemiplegia after a stroke or the like is described. However, the target of the device 10 for rehabilitation, the program 1a for rehabilitation and the rehabilitation method relating to the present invention can be also the patient capable of expressing an intention to voluntarily move the body even slightly.

In this case, after inducing certain measure of the kinesthetic illusion to the patient by the kinesthetic illusion inducing means 2, the patient is made to think of moving the body by his/her own intention. Then, the biological signal acquisition unit 71 detects the characteristic biological signal, and the control signal output unit 73 outputs the control signals to the virtual part driving means 8 in accordance with the detection timing. Thus, the virtual part simulating the rehabilitation target part of the patient is operated in the state of being synchronized with the intention of the patient.

Therefore, by viewing the operation of the virtual part, the kinesthetic illusion of the patient is further increased. That is, the operation of the virtual part by the virtual part driving means 8 becomes the visual stimulation, and achieves a role as the kinesthetic illusion inducing means 2. Note that the control signal output unit 73 may output the control signals also to the body driving means 4 and/or the brain stimulating means 5 simultaneously with the output of the control signals to the virtual part driving means 8.

In addition, the control signal output unit 73 can also control the moving amount of the virtual part by the virtual part driving means 8 according to the characteristic amount of the characteristic biological signal. Thus, the patient can be provided with visual feedback such as urging the patient to make an effort to strengthen the intention to move the body when the moving amount of the virtual part is small, and the rehabilitation effect is improved.

Further, the target patient of the device 10 for rehabilitation, the program 1*a* for rehabilitation and the rehabilitation method relating to the present invention is not limited to the above-described patient with hemiplegia or the like. For example, the patient with pain that remains after an injured part is healed such as phantom limb pain of feeling the pain in cut-off limbs after the limbs are cut off due to injury or sickness or the pain that chronically remains at a local part (such as limbs) after rest of the part is forced due to the injury such as a bone fracture may be a target.

In this case, by executing the rehabilitation using the device 10 for rehabilitation, the program 1*a* for rehabilitation and the rehabilitation method relating to the present invention with the injured part of the patient as the rehabilitation target part, the effect that the pain that remains at the part is reduced or made to disappear is expected.

According to the present embodiment as described above, the following effects are demonstrated.

1. The kinesthetic illusion is induced even to the patient incapable of expressing the intention to voluntarily move the body, and the high rehabilitation effect can be obtained.
2. Training for effectively recovering the motor function of the patient with hemiplegia after a stroke or the like can be executed.
3. The patient only needs to rest and non-invasive rehabilitation with less burdens on the patient can be performed.
4. The timing at which the kinesthetic illusion is induced and the timing of driving the body driving means 4 and the brain stimulating means 5 can be highly accurately synchronized.
5. The kinesthetic illusion can be effectively induced, and the induction can be highly accurately detected.
6. Drive of the body driving means 4 and the brain stimulating means 5 in the state where the kinesthetic illusion is not induced is suppressed, and burdens on the patient can be reduced.
7. The pain that remains after an injured part is healed such as phantom limb pain can be reduced or made to disappear.
8. For the patient capable of slightly expressing the intention to voluntarily move the body, by controlling feedback of the operation of the virtual part and repeatedly looping the induction of the kinesthetic illusion and the drive of the virtual part, the high rehabilitation effect can be obtained.

Next, specific examples of the device 10 for rehabilitation, the rehabilitation system 1 including it, the program 1*a* for rehabilitation and the rehabilitation method relating to the present invention will be described.

EXAMPLE 1

In the present example 1, an experiment of confirming how the brain activity changes in the case of imparting brain stimulation in the state of inducing the kinesthetic illusion and in the case of imparting the brain stimulation in the state of not inducing the kinesthetic illusion was conducted.

First, as a condition of inducing the kinesthetic illusion (illusion condition), as illustrated in FIG. 5(*a*), a liquid crystal monitor was installed so as not to be in contact at a left forearm part of a completely resting subject. On the liquid crystal monitor, the video image for the visual stimulation in which an index finger (pointing finger) of the left forearm of another person repeats abduction/adduction movements was projected. Then, an installation position of the liquid crystal monitor was adjusted such that the left forearm (virtual part) inside the video image for the visual stimulation and the left forearm (rehabilitation target part) of the subject appeared to overlap.

On the other hand, as a condition of not inducing the kinesthetic illusion (non-illusion condition), as illustrated in FIG. 5(*b*), the liquid crystal monitor displaying the virtual part was separately installed such that the left forearm of the subject himself/herself could be seen. Then, while recognizing that his/her own index finger was not moving, the same video image for the visual stimulation as above was projected.

Under the above-described two conditions and the condition of the resting time respectively, the motor evoked potential (MEP) to be an index of the excitability of the brain was recorded for the subject, using an EMG/evoked potential inspection device (NIHON KOHDEN CORPORATION, Neuropack).

Specifically, at a position suitable for recording the motor evoked potential from a left finger, the transcranial magnetic stimulation (TMS) was conducted using a circular coil. A stimulus intensity of the transcranial magnetic stimulation was 114.61±7.91% of a resting time movement threshold as a result of searching an appropriate test stimulus intensity for each subject. In addition, the transcranial magnetic stimulation was executed in accordance with the timing at which the left index finger made the abduction movement in the video image for the visual stimulation. Note that the motor evoked potential was recorded also from an abductor digiti minimi muscle (ADM) other than a first dorsal interosseous muscle (FDI) which is the muscle relating to the abduction movement of the index finger.

Superimposed waveforms of the motor evoked potential recorded under the above individual conditions are illustrated in FIG. 6. As illustrated in FIG. 6, under the illusion condition that the kinesthetic illusion was induced, an amplitude of the motor evoked potential was clearly larger than that of the motor evoked potential under the resting time and non-illusion conditions. That is, it was clearly indicated that the excitability of a corticospinal tract was increased under the illusion condition.

According to the present example 1 as above, it was indicated that the brain activity is activated when the brain stimulation is given in the state where the kinesthetic illusion is induced and the brain activity is not activated even when the brain stimulation is given in the state where the kinesthetic illusion is not induced. In addition, it was indicated that, since the movement is not learned in the state of the low brain activity, even when the body is moved by the body driving means 4 or the brain is stimulated by the brain stimulating means 5 blindly, the high rehabilitation effect cannot be obtained. That is, it was made clear that, as in the present invention, an order of inducing the kinesthetic illusion first and driving the body and stimulating the brain in accordance with the timing is extremely important.

Note that, in the present example 1, facilitation of the motor evoked potential in a dominating area of the first dorsal interosseous muscle did not occur during the adduction movement, and it did not occur in the motor evoked potential evoked from a dominating area of the abductor digiti minimi muscle either. Further, under the non-illusion condition that the installation position of the monitor was shifted though the same moving image was being looked at and it was visible that his/her own finger was not moving, there was no change in the motor evoked potential. Therefore, it can be understood that the illusion condition is a facilitation phenomenon induced with movement direction dependency and body part selectivity like actual movements.

EXAMPLE 2

In the present example 2, an experiment of confirming in which band of the frequency components of the brain waves the characteristic brain activity due to the induction of the kinesthetic illusion appears was conducted.

First, a condition of detecting the characteristic brain activity (illusion condition) was turned to an experimental condition similar to the example 1. However, as the video image for the visual stimulation, a moving image in which a hand joint as the rehabilitation target part of a subject (24 years old, male) repeated palmar flexion was used. In addition, the subject was made to have an image that the hand joint repeated the palmar flexion in the head in accordance with the video image for the visual stimulation.

On the other hand, as a condition of not detecting the characteristic brain activity (non-illusion condition), without changing the position of the liquid crystal monitor from the position under the illusion condition, the moving image itself was vertically inverted and displayed such that the virtual part inside the video image for the visual stimulation and the rehabilitation target part of the subject do not overlap.

Under the above-described two conditions respectively, from a point of time one second before starting the reproduction of the video image for the visual stimulation, the signal strength in each frequency component was measured, using the EMG/evoked potential inspection device (NIHON KOHDEN CORPORATION, Neuropack). The result is illustrated in FIG. 7.

As illustrated in FIG. 7, when the illusion condition and the non-illusion condition were compared, a large difference was observed in the change of the signal strength near 10 Hz, immediately after the video image for the visual stimulation was started. Then, the signal strength in the frequency band of 8 to 13 Hz, which is generally used as the frequency component relating to the movement, is extracted under the individual conditions, and a time change of the average value which is made into a graph is illustrated in FIG. 8.

As illustrated in FIG. 8, under the illusion condition, when the video image for the visual stimulation was started, the signal strength drastically increased, and drastically decreased thereafter. On the other hand, under the non-illusion condition, tendency slightly similar to the illusion condition was observed after the start of the video image for the visual stimulation, but it was not an extreme change.

According to the present embodiment 2 as above, it was indicated that the characteristic brain activity due to the induction of the kinesthetic illusion appears in the predetermined frequency band in the brain waves.

EXAMPLE 3

In the present example 3, an experiment of confirming how the motor evoked potential to be the index of the excitability of the brain changes before and after imparting the various stimulation was conducted.

Specifically, as the stimulation to a healthy subject, the following three kinds were set.

Stimulation 1: Imparting the transcranial stimulation by direct current (transcranial direct current stimulation)

Stimulation 2: Making the subject have an image that his/her own body is moving in the head Stimulation 3: Showing the video image for the visual stimulation for imparting the visual stimulation Then, the three kinds of the stimulation described above were combined and the following five stimulation conditions were set.

Stimulation condition 1: Stimulation 1+stimulation 2+stimulation 3

Stimulation condition 2: Stimulation 1 only

Stimulation condition 3: Stimulation 1+stimulation 2

Stimulation condition 4: Stimulation 1+stimulation 3

Stimulation condition 5: Stimulation 2+stimulation 3

The stimulation was given for 10 to 15 minutes under the individual stimulation conditions described above, and a change rate of the motor evoked potential was measured using the EMG/evoked potential inspection device (NIHON KOHDEN CORPORATION, Neuropack) from the stimulation start to 60 minutes after the stimulation end. The time change of the average value of the change rate is illustrated in FIG. 9.

As illustrated in FIG. 9, an F value and a P value of a main effect in a measurement period were $F=14.70$ and $P<0.005$ respectively, and an F value and a P value of interaction were $F=1.964$ and $P=0.027$ respectively. Therefore, according to the present example 3, it was indicated that the motor evoked potential is statistically significantly improved after imparting each stimulation described above.

In addition, in the case of imparting the electrical stimulus alone (stimulation condition 2), as illustrated in FIG. 9, no significant difference was observed in the change rate of the motor evoked potential between the points of time of starting the stimulation and the immediately after ending the stimulation. In contrast, in the case of imparting the electrical stimulus at the timing of inducing the kinesthetic illusion by the video image for the visual stimulation (stimulation condition 4), the change rate of the motor evoked potential indicated a highest value immediately after ending the stimulation, and the excitability of a cortical motor area was significantly increased. Thus, according to the present example 3, it was indicated that the rehabilitation relating to the present invention has a higher acute effect.

Further, in the case of making the subject have an image of moving himself/herself and imparting the electrical stimulus at the timing of inducing the kinesthetic illusion by the video image for the visual stimulation (stimulation condition 1), as illustrated in FIG. 9, the high excitability lasted in the cortical motor area for at least 30 minutes after the stimulation was ended. It is considered that, as the durability is longer, the movement relating to the rehabilitation is more easily learned. Therefore, according to the present example 3, it was indicated that, for the patient capable of even slightly expressing the intention to voluntarily move the body, by synchronizing the intention with the timing at which the kinesthetic illusion is induced, the higher rehabilitation effect can be obtained.

EXAMPLE 4

In the present example 4, an experiment of confirming the brain activity while the kinesthetic illusion is induced by the visual stimulation was conducted.

The subjects were 14 right-handed healthy persons without a clinical history of neurological or mental disorders. Each subject was, as illustrated in FIG. 10, gently fixed so that a position of a right wrist was still in a state of lying on his/her back. In addition, a mirror was fixed before eyes of each subject and a web camera was fixed at a position from which a right hand could be photographed. Then, a state where his/her own right hand projected on a screen on an overhead side by the web camera was visible by the mirror before the eyes was attained.

Next, after confirming that his/her right hand was visible, each subject slowly repeated a palmar flexion movement of the hand joint at a predetermined speed, and it was recorded as the video image for the visual stimulation by the web camera. Subsequently, each subject was instructed not to move the right hand while looking at the video image for the visual stimulation of himself/herself or another person moving at the same position and at the same speed.

As a result, each subject experienced the kinesthetic illusion only when looking at the video image for the visual stimulation of himself/herself, and did not perceive the kinesthetic illusion by the video image for the visual stimulation of another person. In addition, in order to confirm the brain activity of each subject while the visual stimulation was imparted, blood flow dynamics reaction associated with the activity of the brain was visualized by fMRI (functional magnetic resonance imaging) using a 3T whole body imager (MEDSPEC 30/80 AVANCE; Bruker corporation). With the condition of not perceiving the kinesthetic illusion as a contrast, a result when perceiving the kinesthetic illusion is illustrated in FIG. 11.

As illustrated in FIG. 11, similarly to both side insular cortexes and putamens, significant activation was observed at a back side/ventral side of a left premotor area, upper and lower parietal lobules and a right occipitotemporal junction. On the other hand, even though the subject perceived the kinesthetic illusion, no activation was observed in the primary motor area and a somatosensory area.

According to the present example 4 as above, it was indicated that the kinesthetic illusion by the visual stimulation is induced without activating the primary motor area and the sensory area.

EXAMPLE 5

In the present example 5, an experiment of confirming strength of the kinesthetic illusion by the visual stimulation was conducted.

Specifically, a head-mounted display was mounted on the subject as the display device 21, and the moving image in which the hand joint of the right hand of the subject repeated the palmar flexion was reproduced as the video image for the visual stimulation. While looking at the video image for the visual stimulation, the subject was instructed not to move his/her own right hand. In addition, it was instructed to turn the head of the subject in a direction of his/her own right hand in order to induce the body self-owning feeling. An electromyogram of a dorsiflexion muscle and a palmar flexion muscle at the time is illustrated in FIG. 12.

As illustrated in FIG. 12, while the video image for the visual stimulation was reproduced, strong muscle contraction was observed in the dorsiflexion muscle in particular. In addition, even though the subject did not intend to move his/her own right hand at all, a situation of slight palmar flexion of the right hand was actually observed.

According to the present example 5 as above, it was indicated that the kinesthetic illusion induced by the visual stimulation is an extremely strong illusion.

EXAMPLE 6

In the present example 6, an experiment for more enhancing the kinesthetic illusion induced by the visual stimulation was conducted.

Specifically, as illustrated in FIG. 13, a device including a box-shaped device body into which both hands of the patient can be inserted and a display whose inclination angle to the device body is adjustable (body self-owning feeling inducing means serving also as kinesthetic illusion inducing means) was prepared.

First, to the subject, as illustrated in FIG. 13(a), the video image in which an operation that a stick slowly approaches and lightly touches the back of a left hand of the subject is repeated in a predetermined cycle is shown. In the meantime, in synchronism with the timing of touching inside the video image, as illustrated in FIG. 13(b), a similar stick is brought into contact also with the back of the actual left hand of the subject inserted into the device body.

By repeating this operation, it was confirmed that, after the lapse of predetermined time, when only the stick inside the video image approaches the left hand inside the video image, the subject perceives a thrilling and itchy feeling to be felt when the stick approaches his/her actual left hand, and the body self-owning feeling as if the left hand inside the video image is his/her own left hand is induced.

Next, to the subject, as illustrated in FIG. 13(a), the video image in which an animation character of a white bear performs an action of getting attached to the left hand of the subject is shown. In the meantime, in synchronism with the timing at which the white bear inside the video image touches the palm of the left hand inside the video image, as illustrated in FIG. 13(b), cloth like a stuffed toy is brought into contact also with the palm of the actual left hand of the subject inserted into the device body.

By repeating this operation, after the lapse of predetermined time, when only the animation character of the white bear inside the video image approaches the left hand inside the video image, the subject more strongly perceived a real feeling as if the animation character of the white bear approaches his/her actual left hand. Therefore, it was confirmed that the body self-owning feeling as if the left hand inside the video image is his/her own left hand is more enhanced than the body self-owning feeling induced by the stick video image.

After an inducing process and an enhancing process of the body self-owning feeling described above, the moving image in which the hand joint of the left hand of the subject repeats the palmar flexion was displayed as the video image for the visual stimulation, and the kinesthetic illusion was induced. Thus, it was confirmed that the extremely strong kinesthetic illusion is induced to the subject. In addition, it was confirmed that, even when the sensory stimulation is imparted instead of the visual stimulation after the inducing process and the enhancing process of the body self-owning feeling described above, the strong kinesthetic illusion is similarly induced.

According to the present example 6 as above, it was indicated that, by inducing and enhancing the body self-owning feeling separately before inducing the kinesthetic illusion, the stronger kinesthetic illusion can be induced. In addition, when the patient only inserts a hand into the device body, the hand inside the video image is displayed at an overlapping position. Therefore, it was indicated that, since there is no troublesomeness of setting for overlapping the video image and the rehabilitation target part and setting time is not needed, burdens on the patient are reduced. Further, it was indicated that the above-described device functions as the body self-owning feeling inducing means that imparts the stimulation for inducing the body self-owning feeling, and the kinesthetic illusion inducing means that imparts the stimulation for inducing the kinesthetic illusion.

Note that, in the present example 6, the inducing process of the body self-owning feeling and the enhancing process of the body self-owning feeling are both executed, however, either one may be executed. For example, in the case of executing only the enhancing process of the body self-owning feeling, the process functions as the inducing process of the body self-owning feeling.

In addition, in the present example 6 described above, the body self-owning feeling is induced in order to induce the strong kinesthetic illusion, however, it is not always needed to induce the kinesthetic illusion. That is, it is considered that a fixed rehabilitation effect can be obtained in a state where only the body self-owning feeling is induced though the kinesthetic illusion is not induced.

Note that the device 10 for rehabilitation, the rehabilitation system 1 including it, the program 1a for rehabilitation, and the rehabilitation method relating to the present invention are not limited to the embodiment described above, and can be appropriately modified.

For example, in the present embodiment described above, in the case where the kinesthetic illusion inducing means 2 imparts the visual stimulation, the liquid crystal display is overlapped with the rehabilitation target part and continuously shown as a part of the body, however, it is not limited to the configuration. For example, as in the example 5, the head-mounted display may be used. However, in this case, as described above, in order to induce the body self-owning feeling and the kinesthetic illusion, the head (line-of-sight direction) of the patient needs to turn to the direction of his/her rehabilitation target part.

Therefore, for example, a mounting position to mount the rehabilitation target part is determined, and a positional relation between the mounting position and the head of the patient is calculated beforehand. Then, the position and inclination of the head of the patient may be detected by a gyro sensor and an accelerometer, and the appropriate position and direction of the head may be instructed and adjusted based on the detection value. Or, the size and position of the video image for the visual stimulation may be automatically adjusted based on the position and inclination of the head.

In addition, as another example of imparting the visual stimulation, for the patient whose part of the body is cut off or the like, a space of the cut-off part is whitened with steam or dry ice or the like. Then, the whitened space may be utilized as a screen and the video image for the visual stimulation may be projected on the screen by a projector.

Thus, it is considered that the feeling that it is his/her own body further increases and the kinesthetic illusion tends to be induced.

REFERENCE SIGNS LIST 1 rehabilitation system
1a program for rehabilitation
2 kinesthetic illusion inducing means
3 biological signal sampling means
4 body driving means
5 brain stimulating means
6 storage means
7 arithmetic processing means
8 virtual part driving means
10 device for rehabilitation
21 display device
22 video reproducing device
23 vibration device
61 program storage unit
62 detection target frequency storage unit
63 threshold-for-determination storage unit
64 stimulation timing storage unit
71 biological signal acquisition unit
72 characteristic biological signal detection unit
73 control signal output unit

The invention claimed is:

1. A device for rehabilitation used in physical rehabilitation, the device for rehabilitation for a patient who is incapable of expressing an intention to voluntarily move his/her body, the device comprising:
  a biological signal acquisition unit that is configured to acquire biological signals generated from the patient to whom a kinesthetic illusion that his/her own rehabilitation target part is moving is induced by imparting predetermined illusory stimulation by kinesthetic illusion inducing means that is configured to induce the kinesthetic illusion;
  a characteristic biological signal detection unit that is configured to analyze the biological signals and detects a characteristic biological signal indicating a state where the kinesthetic illusion is induced from the analyzed biological signals; and
  a control signal output unit that determines whether the characteristic biological signal is generated within a predetermined amount of time from inducing the kinesthetic illusion and outputs a control signal for controlling at least one of body driving means that is configured to be attached to the rehabilitation target part of the patient and actuated based on the control signal, the body driving means including an actuator that is configured to physically move the rehabilitation target part or an electrical stimulus device that is configured to transmit electric pulses to the rehabilitation target part to cause muscles to contract and to forcedly move the rehabilitation target part, and brain stimulating means that is configured to be attached to the patient's head and actuated based on the control signal to stimulate a brain of the patient, only when the detected characteristic biological signal is generated within a predetermined amount of time from inducing the kinesthetic illusion.

2. The device for rehabilitation according to claim 1, wherein the predetermined illusory stimulation is visual stimulation by displaying a video image that a virtual part simulating the rehabilitation target part performs a predetermined movement thereby being configured to show the video image to the patient.

3. The device for rehabilitation according to claim 1, wherein the predetermined illusory stimulation is sensory stimulation that is configured to vibrate the rehabilitation target part or to stimulate skin of the rehabilitation target part.

4. The device for rehabilitation according to claim 1, further comprising:
body self-owning feeling inducing means that is configured to impart stimulation that is configured to induce a body self-owning feeling that his/her body is his/her own before inducing the kinesthetic illusion by imparting the predetermined illusory stimulation.

5. The device for rehabilitation according to claim 1, wherein the control signal output unit outputs the control signal for controlling virtual part driving means that drives the virtual part simulating the rehabilitation target part, instead of the control signal for controlling the at least one of the body driving means and the brain stimulating means, or together with the control signal for controlling the at least one of the body driving means and the brain stimulating means, when the characteristic biological signal is detected by the characteristic biological signal detection unit.

6. A rehabilitation system comprising:
the device for rehabilitation according to claim 1;
the kinesthetic illusion inducing means that is configured to induce the kinesthetic illusion; and
the at least one of the body driving means and the brain stimulating means.

7. The device for rehabilitation according to claim 1, wherein
the predetermined illusory stimulation includes visual stimulation by displaying a video image that a virtual part simulating the rehabilitation target part performs a predetermined movement thereby being configured to show the video image to the patient and sensory stimulation that is configured to vibrate the rehabilitation target part or to stimulate skin of the rehabilitation target part, and
the visual stimulation and the sensory stimulation are produced at the same time.

8. The device for rehabilitation according to claim 1, wherein the predetermined amount of time is 2 seconds or less.

9. A non-transitory computer-readable recording medium storing a program for rehabilitation used in physical rehabilitation for a patient who is incapable of expressing an intention to voluntarily move his/her body, the program for rehabilitation making a computer function as:
a biological signal acquisition unit that is configured to acquire biological signals generated from the patient induced with a kinesthetic illusion that his/her own rehabilitation target part is moving by imparting predetermined illusory stimulation by kinesthetic illusion inducing means that is configured to induce the kinesthetic illusion;
a characteristic biological signal detection unit that is configured to analyze the biological signals and detects a characteristic biological signal indicating a state where the kinesthetic illusion is induced from the analyzed biological signals;
a control signal output unit that determines whether the characteristic biological signal is generated within a predetermined amount of time from inducing the kinesthetic illusion and outputs a control signal for controlling at least one of body driving means that is configured to be attached to the rehabilitation target part of the patient and actuated based on the control signal, the body driving means including an actuator that is configured to physically move the rehabilitation target part or an electrical stimulus device that is configured to transmit electric pulses to the rehabilitation target part to cause muscles to contract and to forcedly move the rehabilitation target part, and brain stimulating means that is configured to be attached to the patient's head and actuated based on the control signal to stimulate a brain of the patient, only when the detected characteristic biological signal is generated within a predetermined amount of time from inducing the kinesthetic illusion.

10. The non-transitory computer-readable recording medium according to claim 9, wherein
the predetermined illusory stimulation includes visual stimulation by displaying a video image that a virtual part simulating the rehabilitation target part performs a predetermined movement thereby being configured to show the video image to the patient and sensory stimulation that is configured to vibrate the rehabilitation target part or to stimulate skin of the rehabilitation target part, and
the visual stimulation and the sensory stimulation are produced at the same time.

11. The non-transitory computer-readable recording medium to claim 9, wherein the predetermined amount of time is 2 seconds or less.

12. A rehabilitation method used in physical rehabilitation, the rehabilitation method comprising:
determining whether or not a patient is capable of expressing an intention to voluntarily move his/her body;
if it is determined that the patient is capable of expressing an intention to voluntarily move his/her body, inducing the patient with kinesthetic illusion by imparting predetermined illusory stimulation by kinesthetic illusion inducing means while the patient is not moving and is resting, the kinesthetic illusion being a sense that his/her own rehabilitation target part is moving;
acquiring biological signals generated from the patient whose the kinesthetic illusion is induced by the kinesthetic illusion inducing means by a biological signal acquisition unit;
analyzing the biological signals and detecting a characteristic biological signal indicating a state where the kinesthetic illusion is induced from the analyzed biological signals by a characteristic biological signal detection unit;
determining whether the characteristic biological signal is generated within a predetermined amount of time from inducing the kinesthetic illusion;
outputting a control signal when it is determined that the characteristic biological signal is generated within a predetermined amount of time from inducing the kinesthetic illusion;
based on the control signal, actuating at least one of body driving means attached to the rehabilitation target part of the patient to forcedly move the rehabilitation target part and brain stimulating means attached to the patient's head to stimulate a brain of the patient, wherein
the body driving means is actuated to physically move the rehabilitation target part by an actuator or to transmit electric pulses by an electrical stimulus device to the rehabilitation target part to cause muscles to contract.

13. The rehabilitation method according to claim 12, wherein
the predetermined illusory stimulation includes visual stimulation by displaying a video image that a virtual part simulating the rehabilitation target part performs a predetermined movement thereby being configured to show the video image to the patient and sensory stimulation that is configured to vibrate the rehabilitation target part or to stimulate skin of the rehabilitation target part, and
the visual stimulation and the sensory stimulation are produced at the same time.

14. The rehabilitation method according to claim 12, wherein the predetermined amount of time is 2 seconds or less.

15. A device for rehabilitation used in physical rehabilitation, the device for rehabilitation comprising:
a biological signal acquisition unit that is configured to acquire a biological signal from a patient induced with a kinesthetic illusion that his/her own rehabilitation target part is moving by imparting predetermined illusory stimulation by kinesthetic illusion inducing means that is configured to induce the kinesthetic illusion, after imparting stimulation that is configured to induce a body self-owning feeling that his/her body is his/her own by body self-owning feeling inducing means;
a characteristic biological signal detection unit that is configured to analyze the biological signal and detects a characteristic biological signal indicating a state where the kinesthetic illusion is induced; and
a control signal output unit that outputs a control signal for controlling at least one of body driving means that is configured to forcedly move the rehabilitation target part and brain stimulating means that is configured to stimulate the patient's brain, when the characteristic biological signal is detected by the characteristic biological signal detection unit.

16. A non-transitory computer-readable recording medium storing a program for rehabilitation used in physical rehabilitation, the program for rehabilitation making a computer function as:
a biological signal acquisition unit that is configured to acquire a biological signal from a patient induced with a kinesthetic illusion that his/her own rehabilitation target part is moving by imparting predetermined illusory stimulation by kinesthetic illusion inducing means that is configured to induce the kinesthetic illusion, after imparting stimulation that is configured to induce a body self-owning feeling that his/her body is his/her own by body self-owning feeling inducing means;
a characteristic biological signal detection unit that is configured to analyze the biological signal and detects a characteristic biological signal indicating a state where the kinesthetic illusion is induced; and
a control signal output unit that outputs a control signal for controlling at least one of body driving means that is configured to forcedly move the rehabilitation target part and brain stimulating means that is configured to stimulate the patient's brain, when the characteristic biological signal is detected by the characteristic biological signal detection unit.

17. A rehabilitation method used in physical rehabilitation, the rehabilitation method comprising:
imparting stimulation that is configured to induce a body self-owning feeling that his/her body is his/her own by body self-owning feeling inducing means;
after imparting stimulation that is configured to induce a body self-owning feeling, imparting predetermined illusory stimulation by kinesthetic illusion inducing means that is configured to induce the kinesthetic illusion;
analyzing a biological signal and detecting a characteristic biological signal indicating a state where the kinesthetic illusion is induced; and
outputting a control signal for controlling at least one of body driving means that is configured to forcedly move the rehabilitation target part and brain stimulating means that is configured to stimulate the patient's brain, when the characteristic biological signal is detected by the characteristic biological signal detection unit.

* * * * *